United States Patent [19]

Davies et al.

[11] Patent Number: 5,861,516
[45] Date of Patent: Jan. 19, 1999

[54] PROCESS FOR PREPARING AN ANTIFUNGAL AZOLE WITH HYDRAZINO AND AMIDRAZONE INTERMEDIATES

[75] Inventors: Elwyn Peter Davies, Macclesfield; John David Pittam, Crewe; Keith Blakeney Mallion, Knutsford; Nigel Philip Taylor, Wilmslow, all of United Kingdom

[73] Assignee: Zeneca Limited, London, England

[21] Appl. No.: 793,111

[22] PCT Filed: Aug. 1, 1995

[86] PCT No.: PCT/GB95/01815

§ 371 Date: Apr. 9, 1997

§ 102(e) Date: Apr. 9, 1997

[87] PCT Pub. No.: WO96/04256

PCT Pub. Date: Feb. 15, 1996

[30] Foreign Application Priority Data

Aug. 2, 1994 [GB] United Kingdom ................ 9415544

[51] Int. Cl.$^6$ .................................................. C07D 249/08
[52] U.S. Cl. ..................... 548/266.6; 548/267.8; 548/269.2
[58] Field of Search ............... 548/266.6, 267.8, 548/269.2

[56] References Cited

FOREIGN PATENT DOCUMENTS 0 217 552  4/1987  European Pat. Off. .
472 392   2/1992  European Pat. Off. .
174 769   3/1996  European Pat. Off. .

OTHER PUBLICATIONS

Temple, Jr.: "Trizoles 1,2,4" (See IPER).
Boyle et al., "Synthesis and Structure Activity Relationships of a Novel Antifungal Agent, ICI 195,739", Annals of New York Academy of Science,1988, pp. 86–101.
Triazole Antifungal, Drugs of the Future, 1993, pp. 424–427.
Huisgen et al., "Additionen der Nitrilimine an Oxime, Azine und andere CN–Doppelbindungen", Chem. Ber., 1965, pp. 642–649.
Westermann et al., "Über die Umsetzung des Benzloxycar-bonylamino–acedtimidsäure–äthylesters mit Alkyliden–und Arylhydrazinen", Chem. Ber., 1966, pp. 1111–1117.
Chemical Abstract 115:279925a (1991).

*Primary Examiner*—Johann Richter
*Assistant Examiner*—Jane C. Osowecki
*Attorney, Agent, or Firm*—Pillsbury Madison & Sutro, LLP Intellectual Property Group

[57] ABSTRACT

A process for preparing an antifungal azole compound of formula (I) by reacting an epoxide with hydrazine to from a hydrazino compound which is subsequently reacted with an iminoether. The amidrazone product is subsequently reacted with an orthoformate to provide the antifungal azole. The azole, known as ZD0870, shows good activity against human fungal infections including *Candida albicans, Cryptococcus neoformans* and *Aspergillus fumigatus.*

12 Claims, No Drawings

PROCESS FOR PREPARING AN ANTIFUNGAL AZOLE WITH HYDRAZINO AND AMIDRAZONE INTERMEDIATES

This application is the national phase of international application PCT/GB95/01815, filed Aug. 1, 1995 which designated the U.S.

The present invention relates to a chemical process and to intermediates useful in such a process. In particular this invention relates to processes and intermediates for preparing a triazole having antifungal activity.

(+)-(R)-2-(2,4-Difluorophenyl)-1-[3-[(E)-4-(2,2,3,3-tetra-fluoropropoxy)styryl]-1H-1,2,4-triazol-1-yl]-3-(1H-1,2,4-triazol--1-yl)propan-2-ol is a very potent antifungal agent having a broad spectrum of activity. In particular this compound shows good activity against *Candida albicans, Cryptococcus neoformans* and *Aspergillus fumigatus*. This compound is known in the literature by the code D0870 (more recently ZD0870) and has the structure of formula (I):

Representative references in the literature to the antifungal activity of D0870 include Yamada et al., Antimicrobial Agents and Chemotherapy 1993; 37(11): 2412-7; Mochizuki et al., Program and Abstracts of the 33rd Interscience Conference on Antimicrobial Agents and Chemotherapy (ICAAC), New Orleans, 1993, 188 Abs. 377 and Edwards et al., Program and Abstracts of the 33rd Interscience Conference on Antimicrobial Agents and Chemotherapy (ICAAC), New Orleans, 1993, 80 Abs. 143. The compound D0870 and pharmaceutically acceptable salts thereof are described and claimed in European Patent Application Publication no. 472392 and corresponding applications in other territories.

We have now discovered a new process for preparing D0870. This process is particularly suitable for operating on a large scale such as for preparing large quantities of compound for development activities and for sale. This new process avoids the problems associated with the processes disclosed in EPA 472392.

The processes disclosed in EPA 472392 comprise either the reaction of epoxide (A) with 1,2,4-triazole (B) in the presence of sodium hydride or the reaction of the alternative epoxide (C) with a substituted 1,2,4-triazole (D). These processes are depicted in Scheme I below.

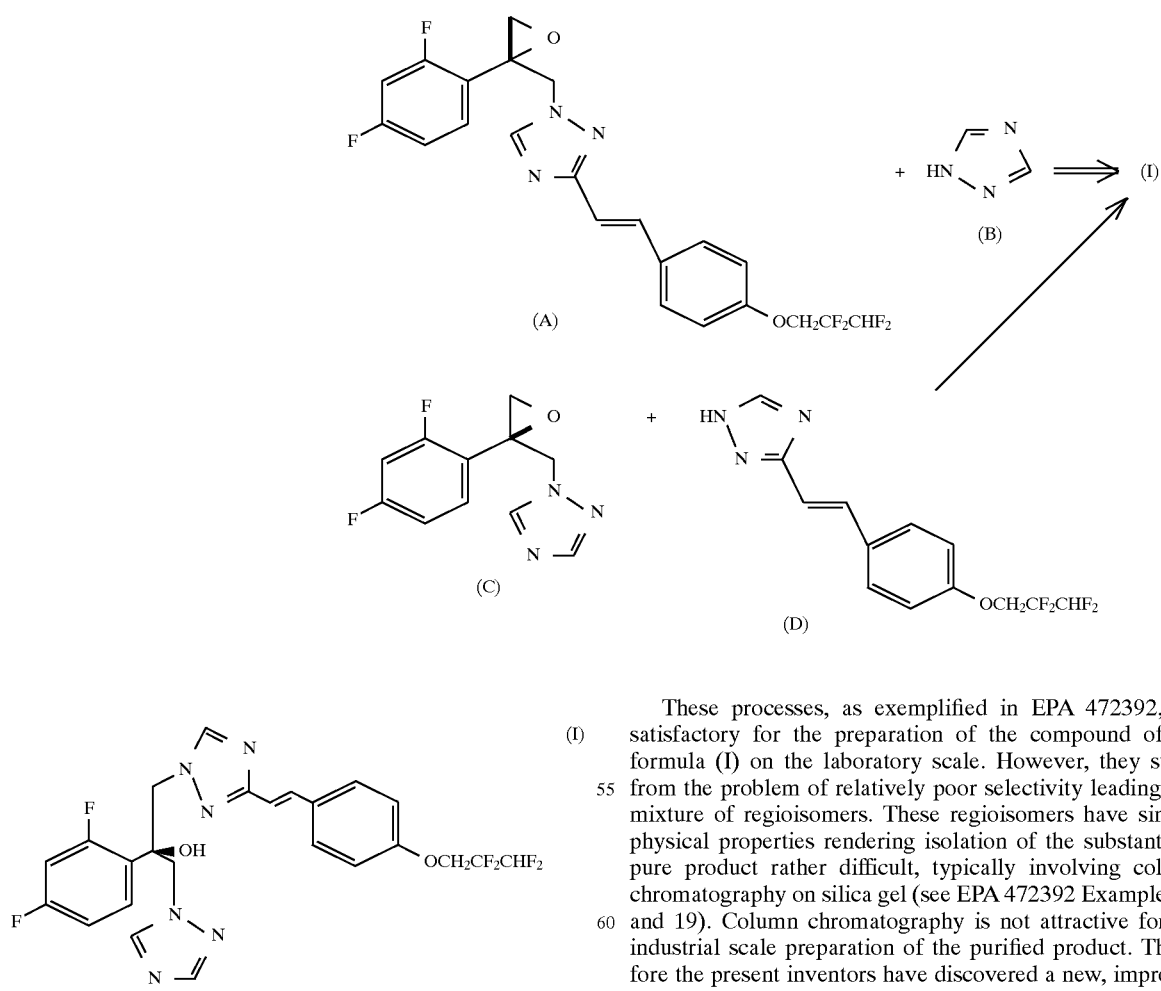

Scheme I

These processes, as exemplified in EPA 472392, are satisfactory for the preparation of the compound of the formula (I) on the laboratory scale. However, they suffer from the problem of relatively poor selectivity leading to a mixture of regioisomers. These regioisomers have similar physical properties rendering isolation of the substantially pure product rather difficult, typically involving column chromatography on silica gel (see EPA 472392 Examples 16 and 19). Column chromatography is not attractive for the industrial scale preparation of the purified product. Therefore the present inventors have discovered a new, improved process which minimises the formation of regioisomers and which removes the need for column chromatography. This is of great significance in operating a practical, industrial scale process. Furthermore the novel process of the present invention provides improved yields. Again, this is of major significance for the economic production of large scale quantities of product.

Our present invention is directed to a new process for preparing D0870 from epoxide (C). In our new process the epoxide (C) is reacted with hydrazine or its equivalent to form a novel hydrazino alcohol intermediate. This novel intermediate is reacted with an iminoether to form a novel amidrazone intermediate which is then cyclised with an orthoformate to provide D0870. Our new process is depicted in Scheme II.

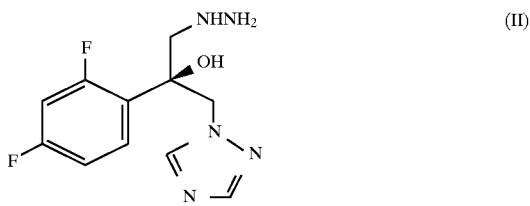

Scheme II

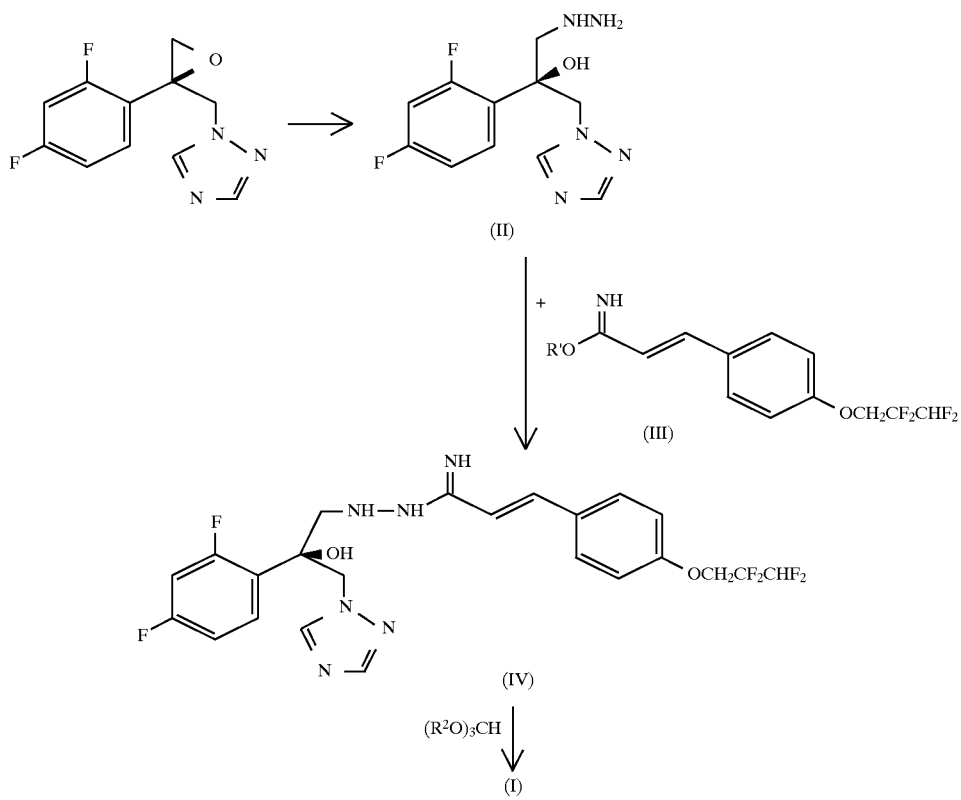

Accordingly the present invention provides a process for preparing a compound of the formula (I) or a pharmaceutically acceptable salt thereof which comprises the steps of:

i) reacting a compound of the formula (C)

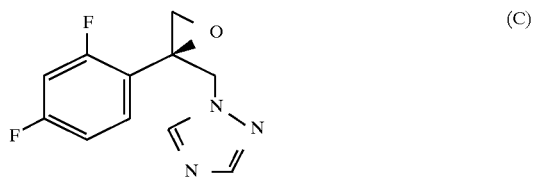

with hydrazine or a chemical equivalent thereof to form a compound of the formula (II):

ii) reacting the compound of the formula (II) with an iminoether of the formula (III) or a chemical equivalent thereof:

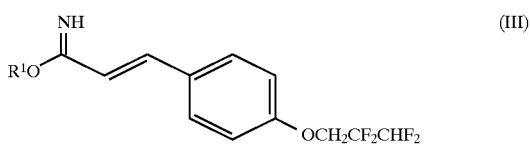

wherein $R^1$ is $C_{1-6}$ alkyl or optionally substituted phenyl; to form a compound of the formula (IV):

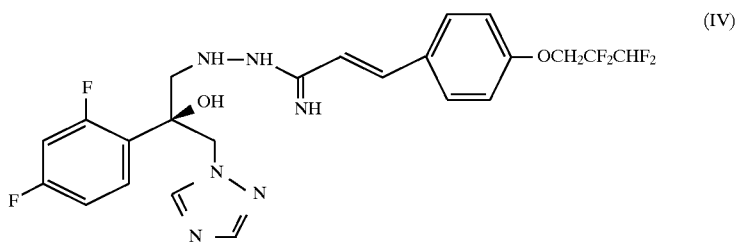

iii) reacting the compound of the formula (IV) with a compound of the formula (V):

$$(R^2O)_3CH \qquad (V)$$

wherein $R^2$ is $C_{1-6}$ alkyl or optionally substituted phenyl; to form a 1–6 compound of the formula (I); and iv) if necessary, forming a pharmaceutically acceptable salt.

The reaction of a compound of the formula (C) with hydrazine or a chemical equivalent thereof is performed under conditions conventional for the ring opening of epoxides. The reaction is typically performed in an organic solvent or mixture of solvents for example toluene or a $C_{1-4}$ alkanol for example isopropanol or isobutanol. The reaction is performed at a non-extreme temperature such as between 0°–60° C. but is preferably performed at approximately ambient temperature for example 15°–35° C., typically about 25° C. The reaction is typically performed in a substantially inert atmosphere for example under nitrogen at normal pressure.

Hydrazine or its chemical equivalent may be used in the reaction. Conveniently hydrazine is present as hydrazine hydrate.

The compound of the formula (C) is known from EPA 472392 wherein it is described in Example 15. It may be introduced into the process of the present invention as isolated material or it may be prepared and reacted in situ. For example it may be prepared from the precursor diol of the formula (VI):

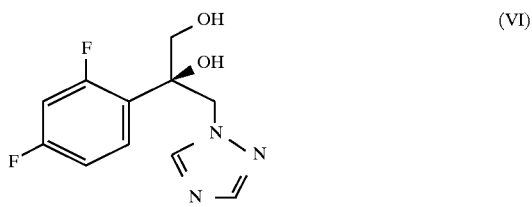

and introduced into the process of the present invention as a solution in toluene or similar solvent. This has been found to be advantageous as it avoids any difficulties associated with the handling of a solid compound of the formula (C).

The compound of the formula (II) is a novel and useful intermediate and forms part of the present invention.

The compound of the formula (II) may be isolated or may be prepared and used in situ or in solution in the next step of the process. Again, use in a solution has been found to be advantageous in order to avoid any difficulties associated with the handling of the solid compound of the formula (II).

The reaction of the compound of the formula (II) and an iminoether of the formula (III) or a chemical equivalent thereof is performed in a substantially inert organic solvent such as a hydrocarbon or $C_{1-4}$ alkanol, preferably an alkanol and most preferably isobutanol. The reaction is performed at a non-extreme temperature such as between 0°–60° C. but is preferably performed at approximately ambient temperature for example 10°–30° C.

The reaction is typically performed in a substantially inert atmosphere for example under nitrogen at normal pressure.

The compound of the formula (IV) may be isolated in any convenient manner. A particular advantage of this intermediate is that it is crystalline. This enables easier isolation and purification of this key novel intermediate.

In the compound of the formula (III), $R^1$ is $C_{1-6}$ alkyl or optionally substituted phenyl. Suitably $R^1$ is methyl, ethyl, propyl or butyl. Preferably $R^1$ is methyl.

The compounds of the formula (III) may be prepared by reaction of a compound of the formula (VII):

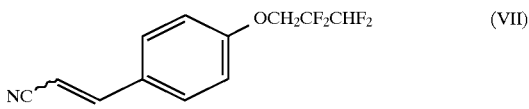

with a compound of the formula $R^1OH$ wherein $R^1$ is as hereinbefore defined. Suitably $R^1OH$ is methanol, ethanol, propanol or butanol. Preferably $R^1OH$ is methanol.

The reaction between the compounds of the formula (VII) and $R^1OH$ is generally performed in an organic solvent or a mixture of organic solvents. Conveniently the solvent, or one of the solvents, is the alcohol $R^1OH$ in excess. A suitable co-solvent, if present, is a hydrocarbon for example toluene. The reaction is conveniently performed at a non-extreme temperature for example $-10°$ C. to $+20°$ C., preferably at about 5° C.

It is necessary that the compound of the formula (III) is provided in the trans or (E)-configuration, as the final product of the formula (I) is in such configuration. Surprisingly we have found that it is not necessary to have the trans or (E)-cinnamonitrile of the formula (VII) in order to obtain the trans or (E)-compound of the formula (III). We have discovered that the compound of the formula (VII) may be in either cis- or trans-configuration; both compounds provide good conversion to the required trans-compound of the formula (III). This is a highly advantageous finding as it removes the necessity of separating cis and trans isomers of the compound of the formula (VII) prior to reaction with $R^1OH$.

The compounds of the formula (III) may be isolated or may be prepared and used in situ. Advantageously, this is prepared as a partially purified solid and is reacted by dissolution in a solution of the compound of the formula (II).

Conveniently the compounds of the formula (VII) may be prepared by reaction of a compound of the formula (VIII):

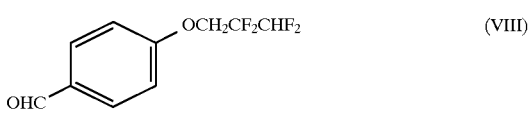

or a protected derivative thereof for example an acetal with a source of $CH_2CN$. Suitably the source of the $CH_2CN$ is a cyanomethylphosphonate for example diethylcyanomethylphosphonate. The reaction is performed in the presence of base. In one aspect the reaction is performed in an aqueous or aqueous-organic medium, the base is water soluble for example a carbonate such as potassium carbonate, and a phase-transfer agent is present to aid dissolution and reaction. The reaction is performed at a non-extreme temperature for example 10°–60° C. for example approximately 40° C.

Typically the compound of the formula (VIII) is formed and reacted in situ from the corresponding nitrile of the formula (IX):

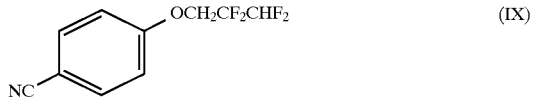 (IX)

by methods conventional for converting nitrites to aldehydes, for example using nickel:aluminium alloy in the presence of acetic acid and heat or using diisobutylaluminium hydride.

The compounds of the formulae (VIII) and (IX) are known from EPA 472392.

The reaction of the compound of the formula (IV) with a compound of the formula (V) is carried out in a substantially inert organic solvent such as a hydrocarbon for example toluene. The reaction generates an alkanol as a by-product and it is convenient to select a solvent that will form an azeotrope with said alkanol permitting ready removal by distillation. Accordingly the reaction is typically performed at a temperature sufficiently elevated to allow azeotropic distillation.

The compound of the formula (V) is suitably trimethyl orthoformate or triethyl orthoformate. Preferably $(R_2O)_3CH$ is triethyl orthoformate.

The product of the formula (I) may be isolated from the reaction mixture in a conventional manner and purified by methods known to those skilled in the art.

Pharmaceutically acceptable salts may be prepared in a conventional manner, for example by treatment of the compound of the formula (I) with the desired acid. Examples of such salts are those prepared with inorganic acids, such as with hydrochloric acid and sulphuric acid and those prepared with strong organic acids such as with p-toluenesulphonic acid and methanesulphonic acid.

The compound of the formula (I) can be made into a variety of drug forms by appropriate selective combination of excipients, binders, lubricants, colourants, flavourings, suspension agents or emulsifiers (for example polysorbate 80 or gum arabic) appropriate types of generally used carriers or solvents, for example sterile water as needed or vegetable oil, and also pharmaceutically acceptable solvents or solution aids (for example alcohol, glycerine or propylene glycol).

As such drug forms, tablets, capsules, granules, microgranules, powders, suppositories, syrups, inhalation drugs, soft ointments, emulsions, suspensions, liquids for eye-drops, aqueous or non-aqueous injectables, emulsion or suspension injectables, or solid injectables used by dissolving, emulsifying or suspending at the time of use, may be mentioned, and may be administered to the patient either orally or parenterally (for example intravenously, intramuscularly, subcutaneously, intrarectally, by percutaneous absorption or transmucosal absorption), or by application in a pessary. In the case of tablets, capsules, powders, injectables, suppositories (systemic) or other systemic administrations, for the daily dosage, calculated in terms of the amount of the compound of the invention, administration of 0.1 mg–2000 mg, preferably 1 mg–200 mg, is desirable, and this can be appropriately varied depending on the condition of the patient. It is also possible to give the whole amount at a single time or to divide it between 2–6 times or to give it as an intravenous drip.

The compound of the formula (I) is a useful antifungal agent and reference is made to EPA 472392 for a description of its properties.

The invention is now illustrated by means of Examples in which:

TW refers to the Twaddle specific gravity scale;
hplc means high performance liquid chromatography;
$^1H$ nmr were recorded at 270 MHz with shifts given in δ(ppm).

EXAMPLE 1

(R)-N-[2-(2.4-Difluorophenyl)-2-hydroxy-3-(E)-(1H-1,2,4-triazol-1-yl)prooyl]-4-(2,2,3,3-tetrafluoropropoxy) cinnamamidrazone (i) (R)-2-(2,4-Difluorophenyl)-3-(1H-1,2,4-triazol-1-yl)propane-1,2-diol (51 g), p-toluenesulphonyl chloride (42 g) and tetrabutylammonium bromide (2 g) were charged to a reaction vessel. Toluene (400 ml) and water (90 ml) were added and the mixture was cooled to 16° C. Sodium hydroxide (27.3 ml; 100° TW) was added, with washing in with water (10 ml). The mixture was stirred vigorously for 1 hour and checked (by hplc) for completion of the reaction. Water (370 ml) was added and, after 20 minutes of stirring, the lower aqueous layer was separated. The interphase was run off with the aqueous layer. The aqueous layer was extracted with toluene, stirred for 15 minutes and allowed to settle for 15 minutes. The aqueous layer was separated retaining the interphase with the organic layer. The organic extracts were combined, stirred with water (100 ml) for 15 minutes, filtered through diatomaceous earth (1 g), washed through with toluene (25 ml) and separated.

The upper organic layer was distilled to about 100 ml volume at approximately 20 mmHg pressure with a bath temperature at a maximum of 40° C.

This procedure provided a solution of (R)-1-[2-(2,4-difluorophenyl)oxiran-2-ylmethyl]-1H-1,2,4-triazole [Compound (C)].

ii) Isobutanol (200 ml) was added to the solution of compound C (from i) above) at ambient temperature under nitrogen. Subsequently hydrazine hydrate (54 ml) was added, maintaining the temperature at 25° C., washing in with isobutanol (22 ml). The mixture was stirred for 3.5 hours and it was checked (by hplc) that the reaction was complete. The solution was washed with saturated brine (4×58 ml), stirring for 15–30 minutes and allowing to settle for 30 minutes after each wash.

This procedure provided a solution of 2-(2,4-difluorophenyl)-1-hydrazino-3-(1H-1,2,4-triazol-1-yl) propan-2-ol in isobutanol which was used without further isolation.

iii) To 4-(2,2,3,3-tetrafluoropropoxy)cinnamonitrile (44 g cinnamonitrile as ~20% w/v solution to toluene) was added methanol (76 ml) and the solution was cooled to 5° C. The reactor was evacuated, purged with nitrogen 3 times and then re-evacuated. Hydrogen chloride gas was introduced via a balloon, replenishing as necessary over 3 hours. The reaction was allowed to stir under an atmosphere of hydrogen chloride for 16 hours at ambient temperature. Toluene (176 ml) was added and the reaction mixture set for distillation under water pump vacuum with the bath temperature set at 35° C. and distillation was continued to a batch temperature of 25° C. at 70 mBar.

Ethyl acetate (88 ml) was added, the suspension stirred at 30° C. for 30 minutes and then cooled to 5° C. for 30 minutes. The solid was collected on an enclosed filter, washed with cold toluene (50 ml) and dried. The methyl (E)-4-(2,2,3,3-tetrafluoro-propoxy)cinnamimidate hydrochloride product was held on the filter for reaction in part iv) below; ($^1$Hnmr (DMSO-d$_6$) δ: 4.12 (s, 3 H); 4.70 (t, 2 H); 6.97 (m, 2 H); 7.18 (d, 2 H); 7.72 (d, 2 H); 7.95 (d, 1 H); 11.60 (broad s, 1 H).

iv) The hydrazino alcohol solution from part ii) above was added to the cinnamimidate from part iii) above agitating the mixture on the filter until the solid had dissolved (30–60 minutes). The solution was transferred to the reaction vessel and washed through with isobutanol (30 ml). The reaction mixture was stirred for 3 hours under nitrogen and checked for the end of reaction by hplc.

A solution of sodium carbonate (19.2 g) in water (260 ml) was added, the batch was stirred for 10 minutes and then separated.

The upper organic layer was stirred with water (100 ml) and methyl tert-butyl ether (100 ml) for 30 minutes and then separated.

The upper organic layer was distilled to a volume of ~150 ml under vacuum (water pump), at a maximum bath temperature of 35° C. giving a final batch temperature of 28° C. at ~20 mBar.

Xylene (360 ml) was added and the mixture redistilled under vacuum to a volume of approximately 250 ml with a jacket temperature of 40° C. and pressure of ~20 mBar. Cyclohexane (100 ml) was added and the mixture held at 40° C. for 30 minutes before cooling to 20° C. over 2 hours and to 5° C. for 2 hours.

The product was separated by filtration and washed with 1:1 xylene/cyclohexane (80 ml) then cyclohexane (40 ml). The product was dried in a vacuum oven at 45° C. to give (E)-N-[2-(2,4-difluoro-phenyl)-2-hydroxy-3-(1H-1,2,4-triazol-1-yl)propyl]-4-(2,2,3,3-tetrafluoropropoxy)cinnamamidrazone (56.26 g); $^1$Hnmr (DMSO-d$_6$): 3.40 (m, 2H), 4.60 (m, 4H); 5.20 (broad, 1H); 5.65 (broad, 2H); 6.30 (d, 1H), 6.60–7.45 (m, 10H; 7.72 (s, 1H); 8.30 (s, 1H); m.p. 137°–40° C.

EXAMPLE 2

(R)-2-(2,4-Difluorophenyl)-1-(3-[(E)-4-(2,2.3.3-tetrafluoropropoxy)-styryl]-1H-1,2,4-triazol-1-yl)-3-(1H-1,2,4-triazol-1-yl)propan-2-ol The product from Example 1 (52.8 g) was suspended in toluene (285 ml) and agitated at ambient temperature. To this suspension was added triethylorthoformate (17.82 g). The mixture was heated to 100° C. for 2–3 hours allowing the ethanol/toluene azeotrope to be removed by distillation.

The reaction mixture was cooled to 60° C. and cyclohexane (65 ml) was added. The reaction mixture was further cooled to 50° C. for 30 minutes to establish crystallisation whereupon cyclohexane (150 ml) was added. The suspension was cooled to 20° C. over 2 hours and cooled to 5° C. for a further hour. The product was collected by filtration, washed with (1:1) toluene/cyclohexane (90 ml), washed with cyclohexane (50 ml) and dried in vacuo at 45° C. to give the title compound (52.5 g).

This compound (1 part by weight) may be purified in the following manner:

a) suspension in methyl t-butyl ether (10 parts by weight);
b) heating under reflux for 30 minutes to dissolve the solid;
c) cooling to 25° C. over 1 hour;
d) cooling to 5° C. for 2 hours;
e) collecting product by filtration;
f) washing with methyl t-butyl ether (2×1.5 parts by weight);
g) drying in vacuo at 45° C.

and may be further purified as follows:

h) charging compound and pulverised carbon (0.1 parts by weight) to a reactor with industrial methylated spirit (IMS) (5 parts by weight);
i) heating to 55° C.;
j) holding the mixture for 60 minutes;
k) filtering at 50° C. washing through with IMS (1 part by weight);
l) heating to 60° C. with the addition of demineralised water (6 parts by weight);
m) seeding the solution, (with material previously obtained) holding it at 60° C. overnight;
n) programmed temperature recycling followed by cooling to 10° C.;
o) collecting product by filtration, washing through with demineralised water (4 parts by weight);
p) drying to constant weight with hot nitrogen at 45° C. M.pt 125° C.; nmr (CDCl$_3$): 4.25–4.90 (m, 6H); 5.59 (s, 1H); 6.08 (tt, 1H); 6.70–7.00 (m, 3H); 7.35–7.65 (m, 4H); 7.88–8.11 (s,d, 3H).

EXAMPLE 3

Preparation of 4-(2,2.3.3-tetrafluoropropoxy)cinnamonitrile (used in Example 1 iii)

4-(2,2,3,3-Tetrafluoropropoxy)benzonitrile (100.0 g) and 1:1 nickel: aluminium alloy (50.2 g) were agitated in water (215 ml) and the mixture heated to reflux before adding 80% acetic acid (846 ml) over a period of 1 hour. Once the addition was over, agitation and heating were maintained until hplc analysis indicated that the reaction was complete. The mixture was cooled to 80° C. and filtered through diatomaceous earth which was blown fairly dry and washed with water (129 ml), toluene (600 ml), and water (248 ml). The aqueous phase was separated off, extracted with toluene (143 ml), and the combined toluene extracts washed twice with water (2×143 ml) then once with a solution of potassium carbonate (14.3 gms) in water (143 ml) to produce 4-(2,2,3,3-tetrafluoropropoxy)benzaldehyde; $^1$Hnmr (CDCl$_3$): 4.45 (t, 2H); 6.10 (tt, 1H); 7.05 (d, 2H); 7.90 (d, 2H); 9.95 (s, 1H).

To the agitated solution of aldehyde was added water (286 ml). Aliquat 336 (7.0 g) and potassium carbonate (63.7 g). Diethylcyanomethylphosphonate (1.05 equivalents based on aldehyde content) was added and the contents temperature raised to 40° C. When HPLC analysis indicated end of reaction the two phases were allowed to settle, the lower aqueous phase separated and the toluene solution washed with 15% brine (235 ml). The volume of the toluene solution reduced from around (740 ml) to 488 ml by atmospheric distillation to give an approximately 20:80 mixture of cis- and trans- isomers; $^1$Hnmr (DMSO-d$_6$) cis-isomer; 4.70 (t, 2H); 5.75 (d, 1H); 6.70 (tt, 1H); 7.20 (d, 2H); 7.35 (d, 1H); 7.85 (d, 2H): trans-isomer: 4.67 (t, 2H); 6.20 (d, 1H); 6.53 (tt, 1H); 7.15 (d, 2H); 7.55 (d, 1H); 7.70 (d, 2H).

We claim:
1. A process for preparing a compound of the formula (I):

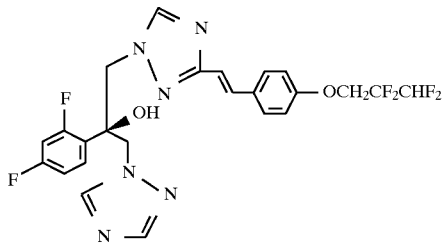

or a pharmaceutically acceptable salt thereof, which comprises:
i) reacting a compound of the formula (C)

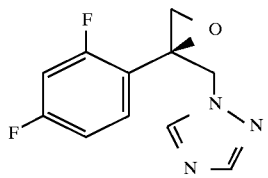

with hydrazine to form a compound of the formula (II):

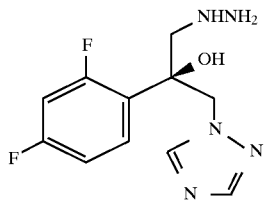

ii) reacting the compound of the formula (II) with an iminoether of the formula (III):

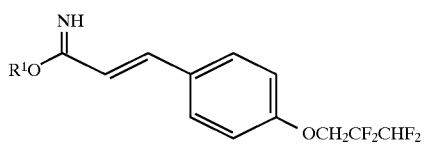

wherein $R^1$ is $C_{1-6}$ alkyl or optionally substituted phenyl; to form a compound of the formula (IV):

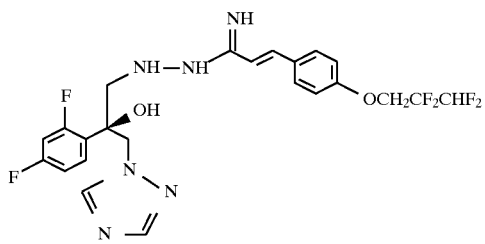

iii) reacting the compound of the formula (IV) with a compound of the formula (V):

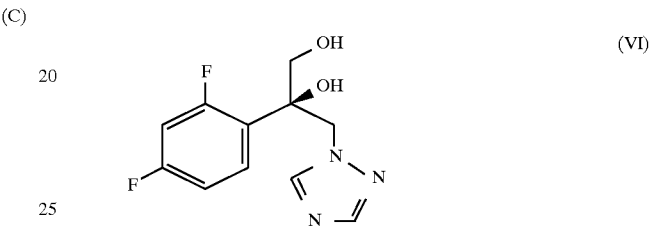

wherein $R^2$ is $C_{1-6}$ alkyl or optionally substituted phenyl; to form a compound of the formula (I); and iv) if necessary, forming a pharmaceutically acceptable salt.

2. A process according to claim 1 wherein the compound of the formula (III) is prepared as a solid and is reacted by dissolution in a solution of a compound of the formula (II).

3. A process according to either claim 1 or claim 2 wherein the compound of the formula (C) is prepared from a compound of the formula (VI):

(VI)

and is reacted as a solution.

4. A process according to claim 1 or 2 wherein the compound of the formula (III) is prepared from a mixture of (E)- and (Z)-4-(2,2,3,3-tetrafluoropropoxy)cinnamonitrile and a $C_{1-6}$ alcohol.

5. A process according to claim 4 wherein the compound of the formula (III) is methyl (E)-4-(2,2,3,3-tetrafluoropropoxy)cinnamimidate hydrochloride.

6. A process according to claim 1 which comprises reacting (R)-1-[2-(2,4-difluorophenyl)oxiran-2-ylmethyl]-1H-1,2,4-triazole with hydrazine hydrate to form 2-(2,4-difluorophenyl)-1-hydrazino-3-(1H-1,2,4-triazol-1-yl)propan-2-ol, reacting this product with methyl (E)-4-(2,2,3,3-tetrafluoropropoxy)cinnamimidate, and subsequently reacting the (E)-N-[2-(2,4-difluorophenyl)-2-hydroxy-3-(1H-1,2,4-triazol-1-yl)propyl]-4-(2,2,3,3-tetrafluoropropoxy)cinnamamidra product with ethyl orthoformate to form (R)-2-(2,4-difluorophenyl)-1-(3-[(E)-4-(2,2,3,3-tetrafluoropropoxy)styryl]-1H-1,2,4-triazol-1-yl)-3-(1H-1,2,4-triazol-1-yl)propan-2-ol.

7. A compound of the formula (IV):

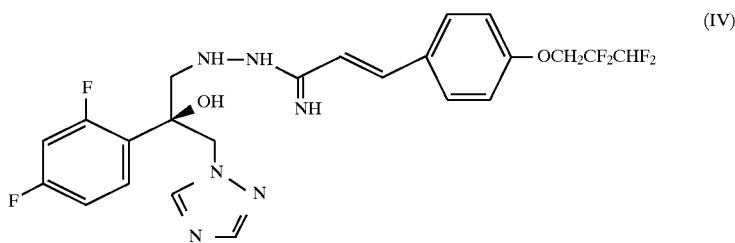

(IV)

8. A compound according to claim 7 when in crystalline form.

9. A compound of the formula (II):

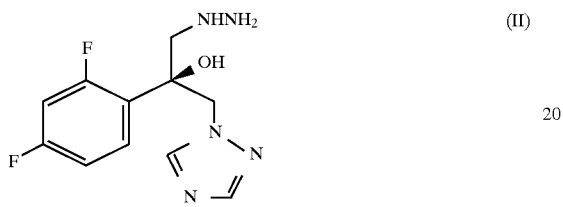

(II)

10. A process for the preparation of a compound of the formula (I):

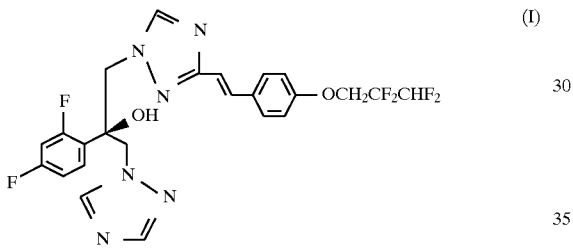

(I)

or a pharmaceutically acceptable salt thereof which comprises reacting a compound of the formula (IV):

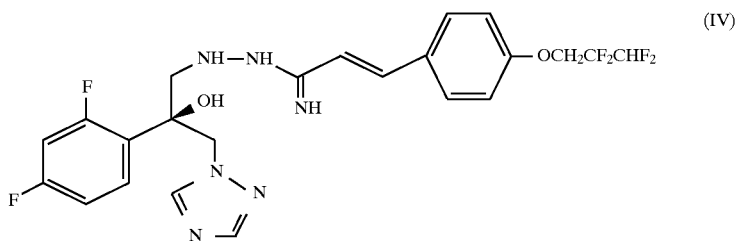

(IV)

with a compound of the formula (V):

(V)

wherein $R^2$ is $C_{1-6}$ alkyl or optionally substituted phenyl; and, if necessary, forming a pharmaceutically acceptable salt.

11. The process of claim 1 wherein said hydrazine is in the form of a hydrazine hydrate.

12. The process of claim 1 wherein said iminoether is in the form of a hydrochloride salt.

* * * * *